United States Patent [19]
Geneen

[11] 3,978,849
[45] Sept. 7, 1976

[54] PULSE RATE INDICATOR

[75] Inventor: Harold S. Geneen, New York, N.Y.

[73] Assignee: International Telephone and Telegraph Corporation, Nutley, N.J.

[22] Filed: Apr. 17, 1975

[21] Appl. No.: 568,884

[52] U.S. Cl. ........................ 128/2.05 T; 128/2.06 F
[51] Int. Cl.[2] ............................................ A61B 5/02
[58] Field of Search .................. 128/2.05 P, 2.05 R, 128/2.05 T, 2.06 A, 2.06 F, 2.06 R

[56] References Cited
UNITED STATES PATENTS

| | | | |
|---|---|---|---|
| 3,384,075 | 5/1968 | Mitchell | 128/2.06 F |
| 3,473,526 | 10/1969 | Herman et al. | 128/2.05 P |
| 3,524,442 | 8/1970 | Horth | 128/2.06 A |
| 3,583,392 | 6/1971 | Frieberger et al. | 128/2.05 R |
| 3,621,844 | 11/1971 | Hayashi et al. | 128/2.06 F |
| 3,706,308 | 12/1972 | John et al. | 128/2.06 F |
| 3,841,315 | 10/1974 | Kopp | 128/2.06 F |

Primary Examiner—William E. Kamm
Attorney, Agent, or Firm—Paul W. Hemminger; John T. O'Halloran

[57] ABSTRACT

A pulse rate indicator automatically indicates a person's pulse rate and changes in this rate. The indicator is individually programmed for each user to account for the overall physiological characteristics of the user. The indicator may be mounted on a wristband and the pulse count is averaged over a time increment, stored and displayed as a reference or rest value. As the user undergoes physical exercise, the subsequent pulse rate is visually indicated and compared with the reference or rest value. When the pulse rate increases, but not to a dangerous level, the color of the indicator changes to inform the user that continued exercise is permissible. When an excessive pulse rate is reached, the indicator changes color and an audible alarm is sounded. The programmable feature therefore allows each person to exercise up to his particular limits for physical fitness tailored to his own physiological makeup, with sufficient advance warning to avoid excessive strain on the heart.

5 Claims, 10 Drawing Figures

Fig. 1 NORMAL

Fig. 2 TACHYCARDIA

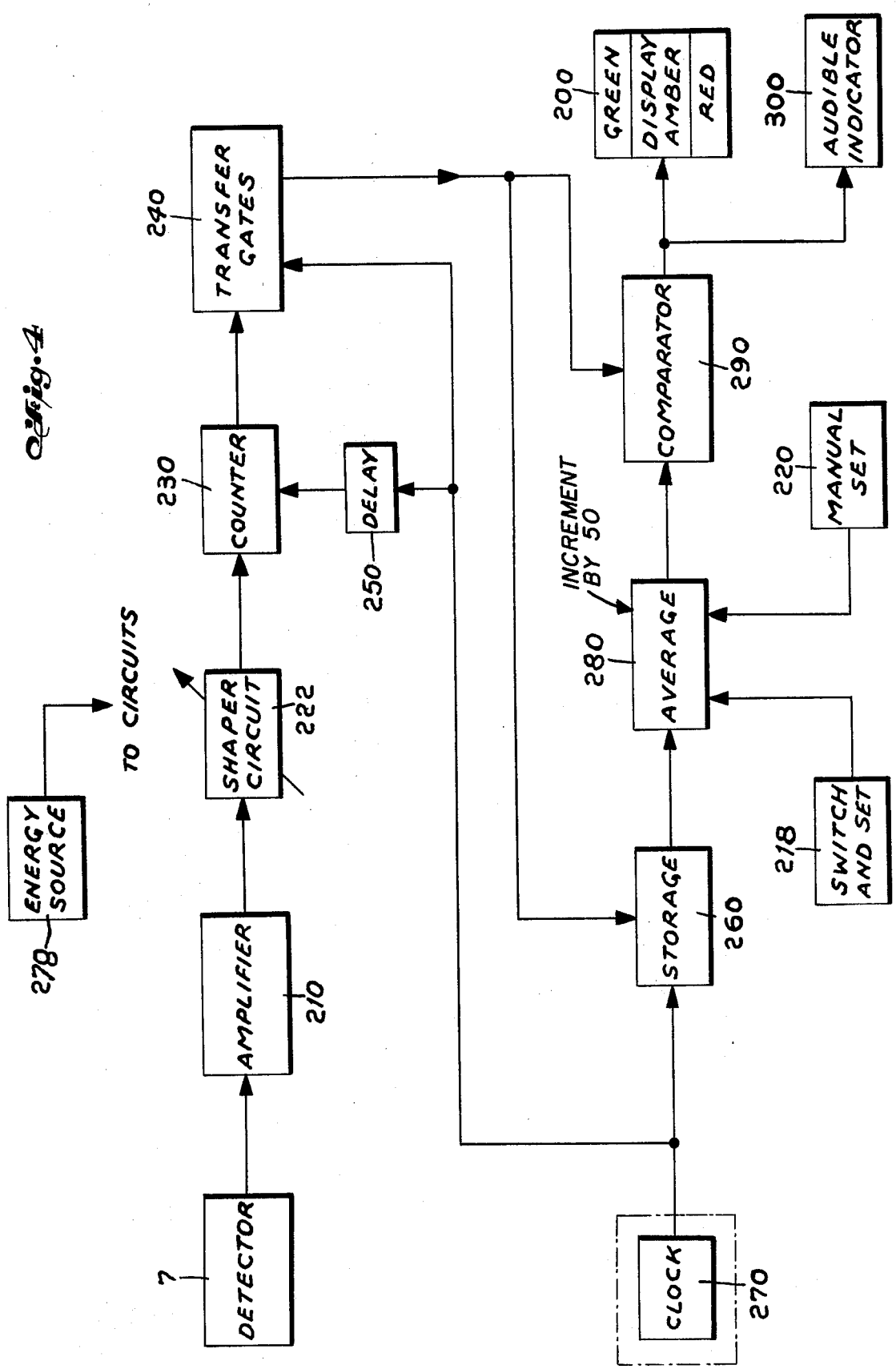

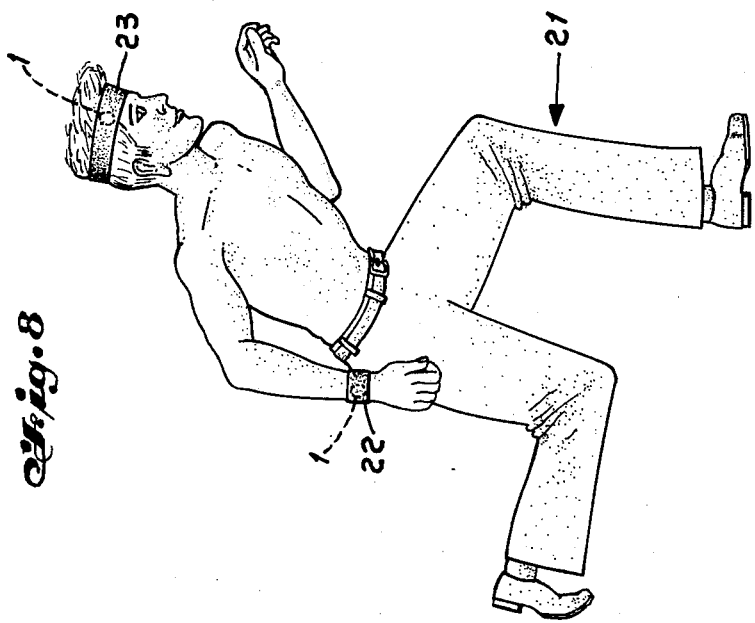
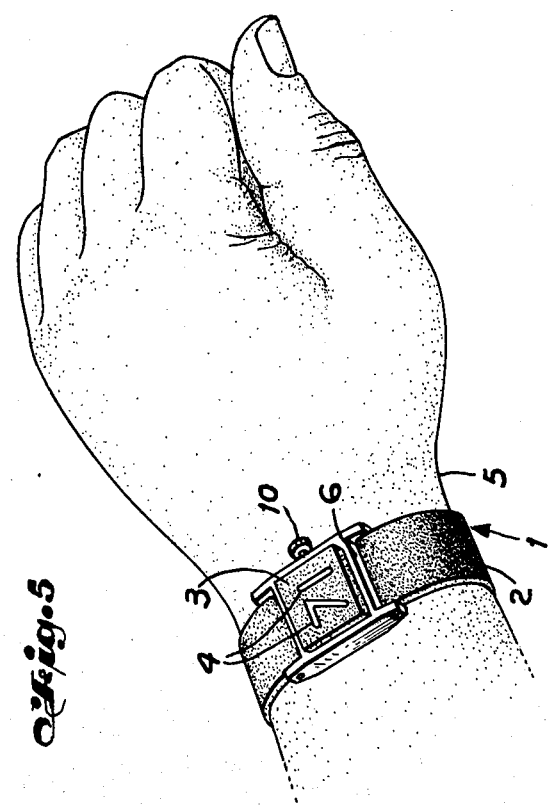
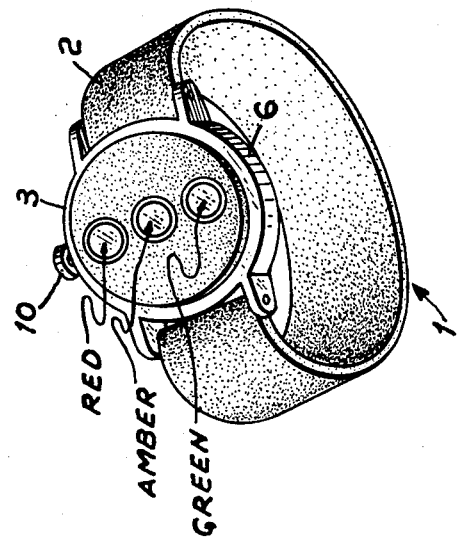
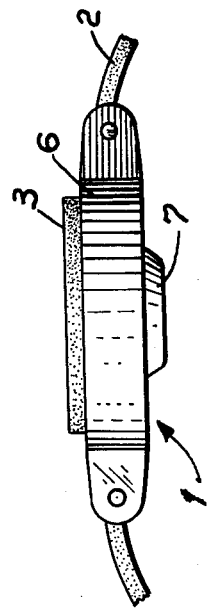

PULSE RATE INDICATOR

BACKGROUND OF THE INVENTION

With the recent advent of aerobic type exercises such as swimming, cycling, jogging and tennis there has been a corresponding upsurge in the rate of deaths relating to cardiovascular exertion. The frequency of heart failures occurring, for example, in winter months due to the exertion on the heart by the over zealous snow shoveler is now occurring throughout the remaining seasons due to heart exertion caused by physical fitness enthusiasts. A person following the current fashion of weight reduction by early morning jogging may lose as much as 20 pounds in a month and may also lose his life. The sudden and continued exertion above a critical limit upon the heart caused by the tremendous amount of blood transport and oxygen consumption required results in a breakdown of the heart structure and, if immediate medical attention is unavailable, death may result. The unfortunate factor common for most cases of coronary failure due to overexertion is that the victim never knows when to stop and death in most cases could have been avoided if the victim didn't continue his exercise.

The heart muscle, like any other vital organ, can build up tolerances to long and continued exertion if given time to develop sufficient cellular structure to accommodate the added workload and to provide for the increased blood handling capacity. By gradually exposing the heart to periods of temporary exertion over increasing periods of time, the body as a whole adapts to a lower oxygen consumption requirement and the heart readily supplies the increased demands for blood flow.

Several devices are currently available for monitoring the pulse rate activity of the human heart. For example, U.S. Pat. No. 3,792,700 describes a technique for indicating the pulse rate of an inactive user by electrodes placed under the armpits of a user. This technique provides an indication of the pulse rate of an inactive user and signals when a coronary problem exists. U.S. Pat. No. 3,802,698 incorporates a pulse rate measuring device with a stationary exercise control system and signals when a particular pulse rate value is reached. U.S. Pat. Nos. 3,742,937; 3,807,388 and 3,863,626 describe miniature pulse monitoring devices that can be worn by persons undergoing physical fitness activities to indicate when a predetermined pulse rate has been exceeded.

The aforementioned examples of the prior pulse rate indicators provide some means for detecting and monitoring the pulse rate of a person undergoing physical exertion and for indicating when the exertion is excessive, but are not tailored to the individual physiological characteristics of the user.

SUMMARY OF THE INVENTION

A pulse rate indicator is mounted to detect the heart pulse rate of a user. The indicator determines the average pulse rate of a user at rest and utilizes this rate as a reference to indicate the pulse rate at a safe exercise level as well as the pulse rate at a dangerous level.

In one embodiment of the invention, the three conditions of pulse rate are displayed in color that is analogous to a traffic control pattern. Consequently, green is selected to represent a rest pulse rate, amber is selected to represent a safe exercise pulse rate level and red represents a dangerous pulse rate level.

In another embodiment of the invention, the pulse rates are digitally displayed in number form as well as in color. Thus, the optimum pulse exercise rate for each individual user is displayed. Since the optimum pulse exercise rate varies from user to user depending on the particular physiological characteristics of each user, the indicator is tailored to each individual user.

Further embodiments utilize an audible alarm to alert the user in a manner analogous to the color display.

BRIEF DESCRIPTION OF THE DRAWINGS

FIG. 1 is a graphic representation of an electrocardiogram display of the surface potential changes of a heart in a person at rest;

FIG. 2 is a graphic representation of an electrocardiogram display of the surface potential changes in a heart in the abnormal condition of tachycardia, which is an excessive heartbeat rate;

FIG. 4 is a schematic circuit diagram of the pulse rate indicator of the instant invention;

FIG. 5 is a top perspective view of one embodiment of the invention wherein the pulse rate is displayed in digital form;

FIG. 6 is a top perspective view of a second embodiment of the invention wherein the pulse rate is displayed in color;

FIG. 7 is a side perspective view of the embodiment of FIG. 6; and

FIG. 8 is a pictorial representation of other embodiments of the invention.

GENERAL DESCRIPTION OF THE INVENTION

Figure 1A:
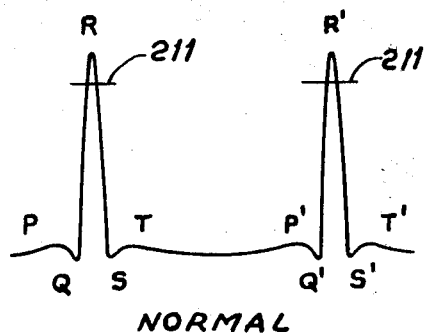
FIG. 1A is a graphic representation of the normal pulse displayed in FIG. 1.
Figure 1A:
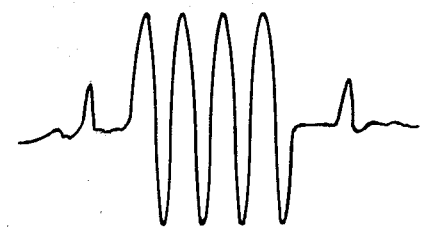
Figure 1A:
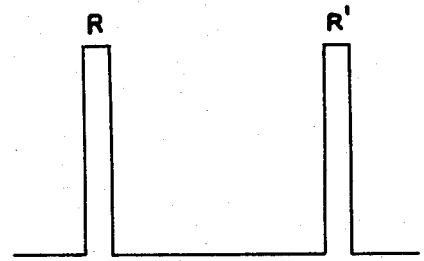

FIG. 1 shows normal pulses as displayed upon an electrocardiogram and with the standard points P Q R S and T indicated. For the purpose of this invention, the pulse rate is defined to be the number of times the R pulse point repeats itself over a given period of time. As shown, R' is the second occurrence of the R pulse point within a short time increment. The medical diagnostician measures the period of time between the occurrences of R and R' as an indication of the condition of a heart. The R pulse rate is related to the pressure exerted by the blood upon one of its chambers, and this in turn is an indication of the pressure exerted by the blood upon the particular artery where the pulse rate is being sensed. It is therefore common in the medical diagnostic field to attach a sensor such as a strain gauge or the like, which is responsive to pressure to produce an electrical pulse having the same frequency and intensity as the pulse shown in FIG. 1. The waveform of FIG. 1A is the electrical counterpart of the pulse R of FIG. 1 and represents the electrical variation in intensity pressure exerted by the heart. The normal pulse rate of FIG. 1 indicates that there is sufficient time between pulse R and pulse R' for the heart to recover in its continuing sequence of expansions and contractions. These expansions and contractions force the blood from one chamber to the other and through the large multiplicity of arteries and veins throughout the body.

FIG. 2 illustrates an electrocardiogram display of a pulse rate in a state of excessive exertion known in the medical field as tachycardia. Here the time between successive pulses is very short and therefore allows the heart muscles very little time to expand and contract to perform the necessary functions of blood transport. The distance between recurrent R pulses therefore is very small and the pulse rate is much higher than the normal condition depicted in FIG. 1.

Figure 2A:
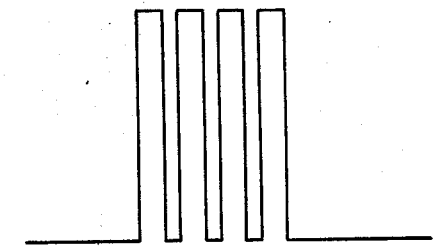
FIG. 2A is a graphic representation of the electrical pulses generated in the circuit of the intant invention representing the abnormal pulse rate as shown in FIG. 2.

FIG. 2A illustrates how the more rapid pulse rate under the condition of tachycardia is translated by this invention into a series of electrical pulses having the same pulse rate frequency as the pulse rate corresponding to the pulse rate occurring within the human body. The normal pulse rate for an adult male is designated as ranging from between 70–72 beats/minute and for an adult female as from 78–82. Pulse rates in both men and women rarely exceed 150 beats/minute in normal everyday activity and pulse rates in excess of 175 beats/minute may be fatal. The condition of tachycardia as portrayed in FIG. 2 corresponds to a pulse rate of 170 beats/minute. The condition of tachycardia therefore presents an excessive burden upon the heart muscle since the heart muscle is required to perform an excessive amount of work in a very short period of time.

The pulse rate for humans varies over a wide range as the human progresses throughout life. Table I, as shown below, illustrates the pulse rate as a function of age where the pulse rate varies from as high as 150 in the early stages of life as to as low as 50 in the seventieth year.

TABLE I

| AGE | PULSE RATE |
| --- | --- |
| Embryo | 150 |
| At Birth | 140–130 |
| First Year | 130–115 |
| Second | 115–100 |
| Third | 100–90 |
| Seventh | 90–85 |
| Fourteenth | 85–80 |
| Fiftieth | 75–70 |
| Seventieth | 65–50 |

Figure 3:
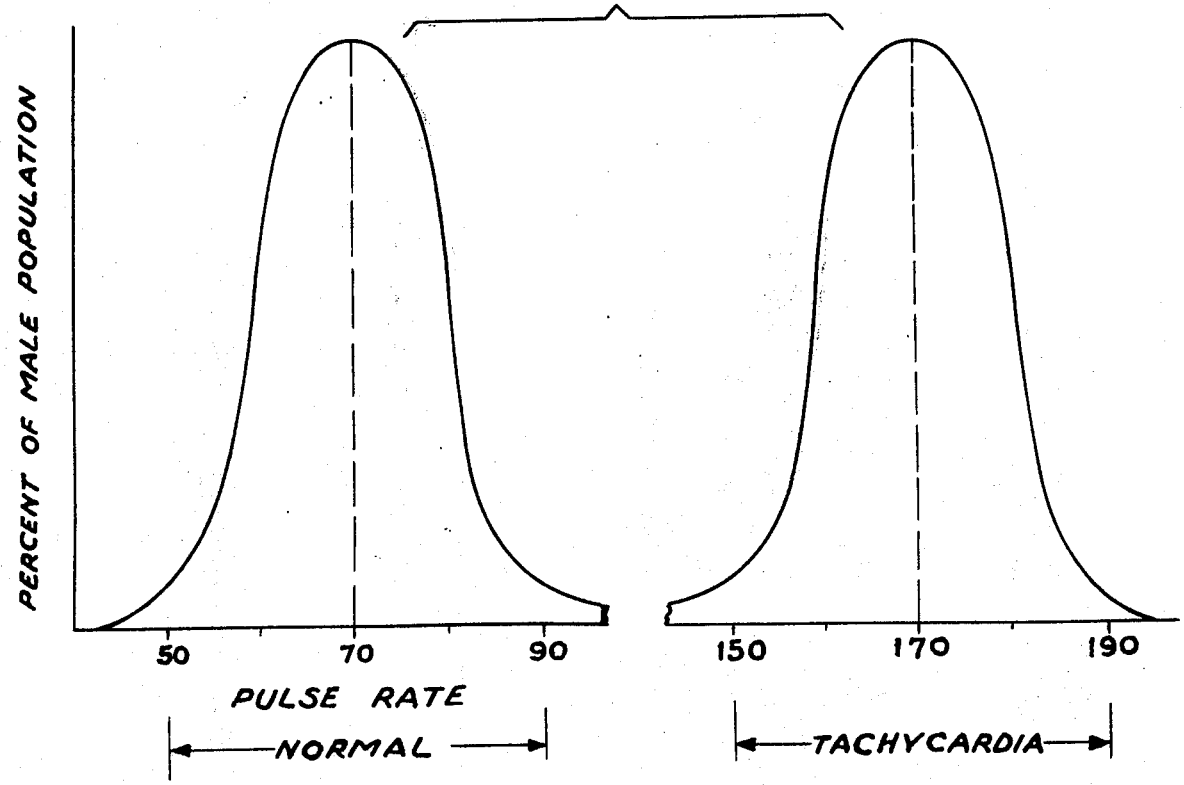
FIG. 3 is a graphic representation of the pulse rate for a normal distribution of male population.

This wide spread in pulse rates is also seen in the adult male population as shown in FIG. 3. Here the pulse rate is illustrated as a bell-shaped distribution of the healthy adult male population. The average pulse rate, for example, is 70 and some men have normal pulse rates as high as 90 and some men have normal pulse rates as low as 50. This distribution of so-called normal pulse rates from 50 to 90 indicates that the pulse rate of every individual must be exactly determined before any type of physical exertion is imparted to the heart. Tachycardia, described earlier as excessive heart pulse rate, occurs at approximately 170 pulses/minute. The person with the lower pulse rate of 50 would have to strain his heart to a substantial degree before the tachycardia pulse rate of 170 would occur. The person with the so-called normal pulse rate of 90 would reach the tachycardia condition of a pulse rate of 170 in a substantially shorter period of time. If a normal distribution is plotted for the onset of tachycardia based on the 170 pulse value then the range in population would be that depicted in FIG. 3. It is evident that persons with higher rest pulse rates would be more prone to the onset of tachycardia than those with lower rest pulse rates. The problem that this invention directs itself to is to determine the accepted pulse rate for exercising that would permit a particular individual to condition his body without excessive strain on the heart and to determine for each particular individual the particular pulse rate at which such physical strain would be excessive.

DETAILED DESCRIPTION OF THE INVENTION

FIG. 5 illustrates one embodiment of the programmable indicator 1 which includes a wristband 2 supporting an indicator face 3 that displays digital pulse rate 4. The indicator 1 is supported on a wrist 5 of a user and the indicator 1 includes a housing 6 that contains the programmable electrical components. The user can at any time see what his pulse rate is during any part of his physical exercise program.

Referring to FIG. 7, the indicator 1 includes a contact type pulse detector 7 which extends from the indicator 1. The detector 7 contacts the radial artery in the vicinity of the user's wrist and relays the detected pulses to the programmable integrated circuit within the housing 6. The pulse detector 7 shown as depending from the indicator 1 can also be part of the wristband 2 since the band would provide a larger surface for detection purposes. The detected pulse rate is digitally displayed upon the viewing indicator face 3.

A traffic control analogy may be utilized to display cnditions of pulse rates. FIG. 6 shows such an embodiment which includes red, amber and green indicating lights on the viewing indicator face 3. The indicator 1 activates the red, amber and green lights in the following manner. When the start and reset knob 10 is depressed energy is supplied by means of a miniature disc-shaped battery contained in the indicator 1 (not shown) and successive heart pulse beats are detected by detector 7 and processed within the indicator 1. The green light indicates that an average rest pulse rate has been determined. This is similar, for example, to the common traffic signal indicator where the green light indicates "go" and the presence of the green light insures the operator that the pulse is being detected and that the battery is operational.

When the user begins to exercise moderately the pulse rate is detected and counted and an optimum exercise pulse rate for the particular average rest pulse rate is determined. For the example given earlier of the medium normal pulse rate of 70, the optimum exercise pulse rate should be 50 greater than the average rest value. Thus, for the 70 rest rate a pulse rate of 120 is the optimum exercise pulse rate for the user and an amber light begins to glow at this rate. The green light would therefore become extinguished at this value and the exerciser is instructed that he has reached the optimum safe exercise pulse rate period. Thus, the optimum safe exercise pulse rate calculated on the basis of 50 beat/minute above the rest value pulse rate indicated by the amber glow continues until a pulse rate of 150 pulses/minute is achieved. At this point the amber light is extinguished and the red light begins to glow indicating to the exerciser that the danger pulse rate condition has been reached and that the exerciser must slow down in order to extinguish the red light and regenerate the amber light.

Table 2, shown below, illustrates the color conditions of green, amber and red along with the corresponding rest, optimum exercise, and dangerous pulse rates for the normal pulse conditions. Although the optimum exercise pulse rate for each group is determined by the addition of 50 pulses or beats/minute above the rest rate, to avoid the onset of tachycardia a red signal is energized to glow at a reduced safety pulse rate of 150 pulses/minute.

TABLE 2

|  | GREEN (Rest Rate) | AMBER (Exercise Rate) | RED (Danger Rate) |
|---|---|---|---|
| Low Normal | 50 | 100 | 150 |
| Normal | 70 | 120 | 150 |
| High Normal | 90 | 140 | 150 |

The color pattern can be utilized in the digital display embodiment shown in FIG. 5. Here the numeric display characters themselves can be caused to glow green, amber or red depending upon the pulse rate condition during exercise. The numerals indicating the average high normal rest rate of 90, in the example of Table 2 can be made to glow green. When the safe optimum exercise rate is reached the numerals glow in an amber color indicating to the user that this particular numerical value is his optimum safe exercise pulse rate. Although higher numerical pulse rates remain amber as exercise continues the user knows that he has exceeded the optimum safe pulse rate and should begin to slow down. If he doesn't slow down, and the pulse rate reaches 150, then numerals indicating this dangerous pulse rate are displayed in red. If he does not slow down at this stage of exercise, the tachycardia may occur.

The visual display indicators depicted in both FIGS. 5 and 6 can have different degrees of light intensity and may have other attention directing characteristics. The amber light, for example, might be caused to blink at the optimum safe exercise pulse rate so that the operator, for example, by looking at the face of the indicator 1 would know that he is exercising within the safe condition of pulse rate. By practice he could pace himself by observing that his particular pulse is beating at the rate of the blinking light. By breaking his stride he could lower his pulse rate to remain at the optimum. Other attention directing means may be incorporated within the indicators of FIGS. 5 and 6 which could include an audible beep device which could be made to vary in frequency in accordance with the pulse rate. The rest condition green, for example, would require no indicating tone and the amber condition would require an auditory beep merely to indicate to the exerciser how fast his pulse rate is going with no possible indication of alarm. The dangerous condition indicated by the pulse rate occurring when the indicator is glowing red would have a rapidly repeating beep and the red light simultaneously could be caused to blink at the same rate to alert the exerciser to slow down.

FIG. 8 depicts alternate embodiments of the pulse sensor of this invention. Here a jogger depicted generally at 21 could carry an indicator unit 1 mounted within a sweatband 23. Here the sensor 7 would contact the vicinity of temporal artery for receiving and recording pulse rates as described earlier. This particular embodiment would require only an audible indicator and the aforementioned red, amber and green indicator lights could be absent. Here the only requirement is that when the pulse rate of 150 is reached then the indicator 1 would begin to beep and the user would summarily have to slacken his pace until the sound disappears. A simplified embodiment is also depicted by the wristband 22. Here again the indicator 1 would contain the same necessary circuit elements to provide an audio beep when the pulse rate detected from the radial artery reaches 150 pulses/minute.

Alternate embodiments within the scope of this invention include audible and visual low pulse level indication when the pulse rate falls below the recorded rest rate average value. This feature would indicate an abnormal physiological condition to the user. Since the pulse rate is lower when sleeping or lying down the long distance driver, for example, would receive an indication that he is starting to doze at the wheel and the audible and visual alarm would alert him of a very dangerous situation.

The digital readout display device of FIG. 5 may serve the health conscious executive who is under a condition of emotional and mental stress even when in a sedentary position at his office. The visual indication of a rising pulse and the occurrence of an amber light in the absence of physical exercise would indicate to the user that his emotions are interferring with his cardiovascular activity. Keeping within the scope and teachings of the instant invention several safety features may be further incorporated within the indicator 1 depicted within the embodiments of FIGS. 5 and 6. Should the exerciser fail to heed the occurrence of the blinking light and the loud and intermittent beep emanating when the pulse rate exceeds 150 then after a time delay the beep is caused to increase in intensity and begin to sound the Morse Code Mayday audio alarm. This would direct a rescuer to the danger, for example, if the user should succumb to heart disease similar to arrythmia and becomes disabled. If the dangerous condition persists for an additional time period then the Mayday distress call also becomes transmitted within the citizens and police broadcast bands in order that immediate help be directed to the stricken individual. The operation of the inventive pulse indicator of FIG. 4 may be explained as follows.

A block diagram of the electric circuit of the indicator is illustrated in FIG. 4. This circuit includes a detector or sensor 7 which may, for example, comprise a thin silicon metal piezoelectric transducer or a piezoelectric strain gauge consisting of barium titanate or barium zirconate. The detector 7 may be attached to the wrist or head of a jogger 21 as designated in FIG. 8 and is included in the indicator 1. The sensor 7 produces an electric output signal as shown in FIGS. 1A and 2A at every pulse beat as shown in FIGS. 1 and 2. The electrical output signal is amplified in the amplifier 210 and then peak detected in the shaper circuit 222. The shaper circuit 222 may, for example, comprise a peak detector and a squarer circuit that detects the peak of the R pulse 211 in the Q R S waveform shown in FIG. 1. The shaper circuit 222 is made variable to tailor it to the individual physiological characteristics of a user because the peak amplitudes of Q R S pulses vary from individual to individual.

The shaped output pulse is applied to a counter 230 where the pulses are counted. At the end of a predetermined period, which may, for example, comprise 15 seconds or alternatively one minute, the count in the counter 230 is transferred through transfer gates 240 to a storage device 260 by a pulse from a clock or timer 270. The clock or timer may, for example, comprise the timer on the wristwatch worn by the jogger. After a slight delay, the counter 230 is reset by the clock 270 via delay 250. The storage device 260 may, for example, comprise a plurality of storage circuits such as shift registers. The count in the first storage circuit is transferred to the second storage circuit when the second count in the counter 230 is transferred through the transfer gates 240 to the storage circuit. At the end of a predetermined number of counts, an averaging circuit 280 adds the pulse counts stored in the storage device 260 and divides by the number of counts to determine the average rest pulse rate over a predetermined period. This average pulse rate is applied to a comparator circuit 290 and displayed in a display device 200. Thus, the display device 200 displays the average or rest pulse rate of the jogger. The display device 200 may, for example, display in green, amber or red and may include light-emitting devices that digitally display the pulse rate. The average rest pulse rate is usually displayed in green.

The averaging circuit 280 also includes a set element 218 to fix or set the average of the pulse rate so that this figure remains constant during jogging. Alternatively, if an individual knows accurately his rest pulse rate, this rate may be set into the averaging circuit 280 by the manual set 220. Both the switch and set element 218 and the manual set 220 are coupled to the knob 10 shown in FIGS. 5 and 6. During the jogging period, the pulse rate is applied through the transfer gates 240 to the comparator 290. The average rest pulse rate stored in the averaging circuit 280 is, as explained previously, incremented by the number 50 to set the optimum safe exercise pulse rates. During a period when exercise is being done, the display device 200 may, for example, digitally display the pulse rate at that particular moment. When the pulse rate reaches the established optimum safe pulse rate number, this number is digitally displayed in amber and an audible indicator 300 may beep as described earlier. When the pulse rate reaches the danger pulse rate of 150 the comparator 290, set to detect this critical number, causes the display device 200 to glow red. Additionally, audible indicator 300 may beep at an increased rate.

The time delay 250 connected to the counter 230 also provides the alternate safety function that when the circuit is first energized by means of knob 10 connecting energy source 278 to the circuit components the time delay 250 will not allow the sensor 7 to energize the aforementioned green light until a sufficient time span has occurred so that a representative average rest pulse rate can be determined. This is important since it is possible that an impatient jogger may upon early waking, when the pulse rate is at its lowest, immediately commence jogging and receive a false amber indication as to the optimum exercise pulse rate since the aforementioned rest rate average was excessively low. The time delay, for example, would give the user adequate time to provide sufficient sample pulse counts to the counter so that a true rest rate pulse average can be determined before the go ahead signal is indicated by means of the aforementioned green light. The components of the circuit depicted in FIG. 4 may comprise an integrated circuit. However, it is not necessary that the detector 7 be directly connected within the circuit. An alternate embodiment, for example, could consist of a sensor which incorporates an ultrasonic transmitter and the other circuit components could be at a remote location from the sensor.

A heavily bundled snow shoveler wearing gloves may be unable to hear the audible alarm indicated from the pulse sensor and audible alarm on the wrist but would clearly hear an audible alarm generated within the sweatband embodiment described earlier as in contact with the temporal artery due to the proximity of the temporal artery and the ear. In the event that the snow shoveler may be reluctant to wear the complete sensor contained within the sweatband similar results could be achieved by locating the detector and transmitter portion of the circuit within a wristband proximate the radial artery and locating a simple receiver in the vicinity of the ear by means of a sweatband or similar device. Here the excessive pulse rate would be detected in the ultrasonic region and regenerated in close proximity to the ear within audible range. It is to be further noted that energy source 278 may be a self-contained battery of the rechargeable type and may provide power to each and every circuit element as required including the green, amber and red display elements which for their purpose of size and efficiency may comprise light emitting diodes.

Although several limited embodiments have been described as operative examples of the inventive pulse rate indicator this is by way of example only and is in no way intended to limit the scope of this invention to these specific examples.

What is claimed is:

1. A body mounted pulse rate indicator comprising in combination: pulse sensing means for detecting heart pulse beats of a wearer and translating said heart pulse beats into corresponding electrical pulses;
   counting means coupled to count said electrical pulses to provide a pulse rate;
   averaging means for determining the average pulse rate of the wearer at rest to establish a rest pulse rate;
   programming means for automatically adding a predetermined increment to said reference pulse rate to denote an optimum safe exercise pulse rate;
   means for setting a predetermined maximum level pulse rate into said indicator to denote a danger level pulse rate; and
   means for continuously comparing the pulse rate at any time to said optimum safe exercise pulse rate and said danger level pulse rate to denote the state of the pulse rate.

2. The combination in accordance with claim 1 that further includes means for displaying said rest pulse rate, said optimum safe exercise pulse rate and said danger level pulse rate in differing indicia.

3. The combination in accordance with claim 2 wherein said differing indicia comprise differing colors.

4. The combination in accordance with claim 3 wherein said differing colors comprise green for said rest pulse rate, amber for said optimum safe exercise pulse rate and red for said danger level pulse rate.

5. The combination in accordance with claim 4 wherein said differing indicia are displayed in numeric form.

* * * * *